US012039636B2

United States Patent
Arberet et al.

(10) Patent No.: US 12,039,636 B2
(45) Date of Patent: Jul. 16, 2024

(54) AGGREGATION BASED ON DEEP SET LEARNING IN MAGNETIC RESONANCE RECONSTRUCTION

(71) Applicant: Siemens Healthineers AG, Forchheim (DE)

(72) Inventors: Simon Arberet, Princeton, NJ (US); Boris Mailhe, Plainsboro, NJ (US); Thomas Benkert, Neunkirchen am Brand (DE); Marcel Dominik Nickel, Herzogenaurach (DE); Mahmoud Mostapha, Princeton, NJ (US); Mariappan S. Nadar, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 443 days.

(21) Appl. No.: 17/473,206

(22) Filed: Sep. 13, 2021

(65) Prior Publication Data

US 2023/0085254 A1    Mar. 16, 2023

(51) Int. Cl.
*G06T 11/00* (2006.01)
*G06N 3/08* (2023.01)
*G16H 30/20* (2018.01)

(52) U.S. Cl.
CPC .............. *G06T 11/003* (2013.01); *G06N 3/08* (2013.01); *G16H 30/20* (2018.01)

(58) Field of Classification Search
CPC ......... G06T 11/003; G16H 30/20; G06N 3/08
See application file for complete search history.

(56) References Cited

U.S. PATENT DOCUMENTS

| 10,460,440 | B2 * | 10/2019 | Zhang | G06T 7/0012 |
| 10,861,165 | B2 * | 12/2020 | Wood | G06V 10/147 |
| 10,996,306 | B2 * | 5/2021 | Heukensfeldt Jansen | G06V 10/993 |
| 11,151,759 | B2 * | 10/2021 | Vija | G01T 1/161 |
| 11,534,136 | B2 * | 12/2022 | Funka-Lea | A61B 8/5261 |
| 11,763,134 | B2 * | 9/2023 | Chen | G06N 3/045 706/15 |

OTHER PUBLICATIONS

Aittala, Miika, and Frédo Durand. "Burst image deblurring using permutation invariant convolutional neural networks." Proceedings of the European Conference on Computer Vision (ECCV). 2018. pp. 1-17.
Wagstaff, Edward, et al. "On the limitations of representing functions on sets." International Conference on Machine Learning. PMLR, 2019. pp. 1-14.
Zaheer, Manzil, et al. "Deep sets." arXiv preprint arXiv:1703.06114 (Apr. 2018). pp. 1-29.

* cited by examiner

*Primary Examiner* — Gregory M Desire

(57) ABSTRACT

For reconstruction in medical imaging using a scan protocol with repetition, a machine learning model is trained for reconstruction of an image for each repetition. Rather than using a loss for that repetition in training, the loss based on an aggregation of images reconstructed from multiple repetitions is used to train the machine learning model. This loss for reconstruction of one repetition based on aggregation of reconstructions for multiple repetitions is based on deep set-based deep learning. The resulting machine-learned model may better reconstruct an image from a given repetition and/or a combined image from multiple repetitions than a model learned from a loss per repetition.

18 Claims, 4 Drawing Sheets

AGGREGATION BASED ON DEEP SET LEARNING IN MAGNETIC RESONANCE RECONSTRUCTION

FIELD

This disclosure relates to medical image reconstruction, such as reconstruction in magnetic resonance (MR) imaging.

BACKGROUND

Some protocols for scanning a patient in medical imaging, such as magnetic resonance (MR), computed tomography (CT), positron emission tomography (PET), or single photon emission computed tomography (SPECT), use repetitious scanning. In MR, multiple repetitions are commonly acquired in diffusion-weighted imaging or turbo-spin-echo imaging, where images reconstructed from each repetition are averaged to decrease the level of noise in the final image. Repetition is also performed in the acquisition of multiple contrasts, for example when acquiring images with different echo times or different flip angles.

The medical imaging uses reconstruction from the scan data to estimate an image or real-space object from measurements. The baseline approach is to reconstruct each repetition separately (e.g., no sharing of information) or to use a sequential regularization (e.g., limited sharing of information, such as performed in reconstruction using compressed sensing with temporal regularization). These reconstructions may be time consuming.

Deep learning (DL) techniques improve the speed and the reconstruction quality compared to traditional reconstruction. Some DL-based image reconstruction methods are based on unrolled iterative algorithms where a data-consistency step alternates with a regularization network. In order to obtain good results, multiple unrolled iterations of reconstruction are performed. Computational time and memory requirements are directly proportional to the number of unrolled iterations. Compressed sensing allows for more rapid scan by reducing the amount of data collected in a given scan. The corresponding approach for reconstruction is not directly applicable to protocols using repetition to gather extra scan data.

SUMMARY

By way of introduction, the preferred embodiments described below include methods, systems, instructions, and computer readable media for reconstruction in medical imaging using a scan protocol with repetition. A machine learning model is trained for reconstruction of an image for each repetition. Rather than using a loss for that repetition in training, the loss based on an aggregation of images reconstructed from multiple repetitions is used to train the machine learning model. This loss for reconstruction of one repetition based on aggregation of reconstructions for multiple repetitions is based on deep set-based deep learning. The resulting machine-learned model may better reconstruct an image from a given repetition and/or a combined image from multiple repetitions than a model learned from a loss per repetition.

In a first aspect, a method of machine training for magnetic resonance (MR) reconstruction in medical imaging is provided. Training data for an MR protocol using multiple repetitions is acquired. A neural network is machine trained for the MR reconstruction using the training data. The neural network is trained for the MR reconstruction to output an image for each one of the multiple repetitions. A first loss used in the training is based on an aggregation of the images from the multiple repetitions. The neural network as machine trained is stored.

In one embodiment, the machine training includes training the neural network to output the image for each one of the multiple repetitions independently of the output for other ones of the multiple repetitions. In another embodiment, the machine training includes training the neural network to output the image for at least one of the multiple repetitions in dependence on information from the neural network used to output an image for another one of the multiple repetitions. The dependence may be a global pooling across instances of the neural network for respective ones of the multiple repetitions.

The MR protocol may be a diffusion-weighted, turbo-spin-echo, contrast with different echo times, or contrast with different flip angles protocol. Other protocols for a given scan of a patient using repetition of scans may be used.

Using the deepset approach in the machine training, the invariance by permutation with respect to the multiple repetitions is preserved. The aggregation used for generating the image from which loss is calculated in the machine training may be an average, a geometric product, or a geometric mean.

In one embodiment, the neural network has an input layer configured to accept information for a single one of the multiple repetitions for the output of the image for that single one of the multiple repetitions. The same neural network is trained to be used in reconstruction for each repetition by input of the scan data for the single repetition at a time. The input layer may include separate inputs or channels for different directions or contrasts. The training is to output the image from the different directions or contrasts for each of the multiple repetitions. Joint losses may be used, such as the first loss based on the aggregation and a repetition loss for each of the different directions or contrasts of each of the multiple repetitions. In other embodiments, the joint loss is used without multiple channel input, such as applying a joint loss of the first loss based on the aggregation and a repetition loss for each image for each of the multiple repetitions.

The use of a loss from the aggregation despite training for reconstruction from one repetition couples the repetitions to each other. Machine training with the first loss includes a measure of difference between the aggregation of the images and a ground truth image such that the neural network learns, for each of the multiple repetitions, based on the aggregation across the multiple repetitions.

In a second aspect, a method is provided for reconstruction of a medical image in a medical imaging system. The medical imaging system scans a patient, resulting in measurements over a series of scans of an imaging protocol. An image processor reconstructs, applying a machine-learned model, a scan image for each of the scans of the series. The machine-learned model was trained for use for each scan of the imaging protocol based on a loss function from a combination of training images from different scans for the imaging protocol. The scan images are combined into the medical image, which is displayed.

In one embodiment, the scanning is magnetic resonance scanning with the imaging protocol comprising a diffusion-weighted imaging protocol or a turbo-spin-echo imaging protocol. The combination used to train is an average.

Repetition imaging using a machine-learned model to aid in reconstruction for each given repetition separately or by sub-groups allows the reconstruction of a scan image for one of the scans of the series to occur prior to the scanning for another of the scans of the series.

In a third aspect, a system is provided for reconstruction in medical imaging. A medical scanner is configured to repetitively scan a region of a patient pursuant to a protocol. The scan provides scan data in repetitions of the protocol. An image processor is configured to reconstruct, for each of the repetitions, a representation of the region. The image processor is configured to reconstruct by application of a machine-learned model having been trained for the reconstruction for each of the repetitions based on a loss function between an aggregate of outputs from the repetitions of the protocol and a ground truth. The image processor is further configured to combine the representations from the repetitions. A display is configured to display an image of the region from the combined representations.

In one embodiment, the medical scanner is a magnetic resonance scanner. The protocol is a diffusion-weighted, turbo-spin-echo, or contrast protocol, and the combination of representations is a sum, a geometric mean, or a geometric product.

In other embodiments, the machine-learned model is a neural network. The neural network is repetitively used for the repetitions as a function in a deep set.

In yet other embodiments, the loss function is a joint loss of first and second losses, the first loss being between the aggregate and the ground truth and the second loss being between one of the representations for one of the repetitions and another ground truth.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

In some medical imaging protocols, repetition is used to collect, at least in part, redundant information. These repetitions, averages, or contrasts are referred to as repetitions. Rather than reconstructing each repetition independently from each other, it may be more advantageous to leverage the common or redundant information shared between the different repetitions of the same scan.

One approach to exploit this redundant information in the context of a deep-learning reconstruction is to add the repetitions in the channel dimension. Extra input channels are provided for inputting the scan data from the different repetitions into the machine learning model (e.g., network) at the same time. However, this implicitly treats the repetitions in an ordered way. The different repetitions of the same scan can be considered independent from each other in the sense that the order in which they are acquired doesn't matter. Adding the repetitions in the channel dimension misses the property of invariance by permutation of these repetitions and thus misses the opportunity to decrease the dimensionality and the complexity of the reconstruction problem.

Instead of creating one multi-channel network to learn to contribute to reconstruction from the scan data of all repetitions at once, a network is trained to contribute to reconstruction for each repetition. For example, a deep-learning network is trained for reconstruction of multiple repetitions (e.g., in sequence or parallel) and is trained in a way to exploit the invariance by permutations of the repetitions. The repetitions are treated as a set both during the training and during inference. This is based deep sets, where it is proved that basically any function defined on a set can be sum-decomposable, i.e., can be written as:

$$f(x) = \rho(\Sigma_{x \in X} \phi(x)) \qquad \text{Eq (1)}$$

for some suitable functions $\rho$ and $\phi$. Based on this argument, an architecture is established where each repetition is fed into a neural network to provide a repetition reconstruction, then the results of the individual repetition reconstructions are aggregated in some way (e.g., the sum of equation 1) and then a loss function such as e.g., L1 is computed on the aggregated result as the function $\rho$.

This approach exploits a coupling between the different repetition reconstructions while preserving the property of invariance by permutation of the repetitions. The network is trained to contribute to reconstruction for any given repetition, but the learned parameters of the network have values informed by the loss based on the aggregation across repetitions. This aggregated loss approach improves performance of the reconstruction as compared to training each repetition separately. The resulting reconstructed image may have more detail, sharpness, and better noise texture based on training using aggregated loss as compared to individual deep learning reconstruction by repetition.

Figure 1:
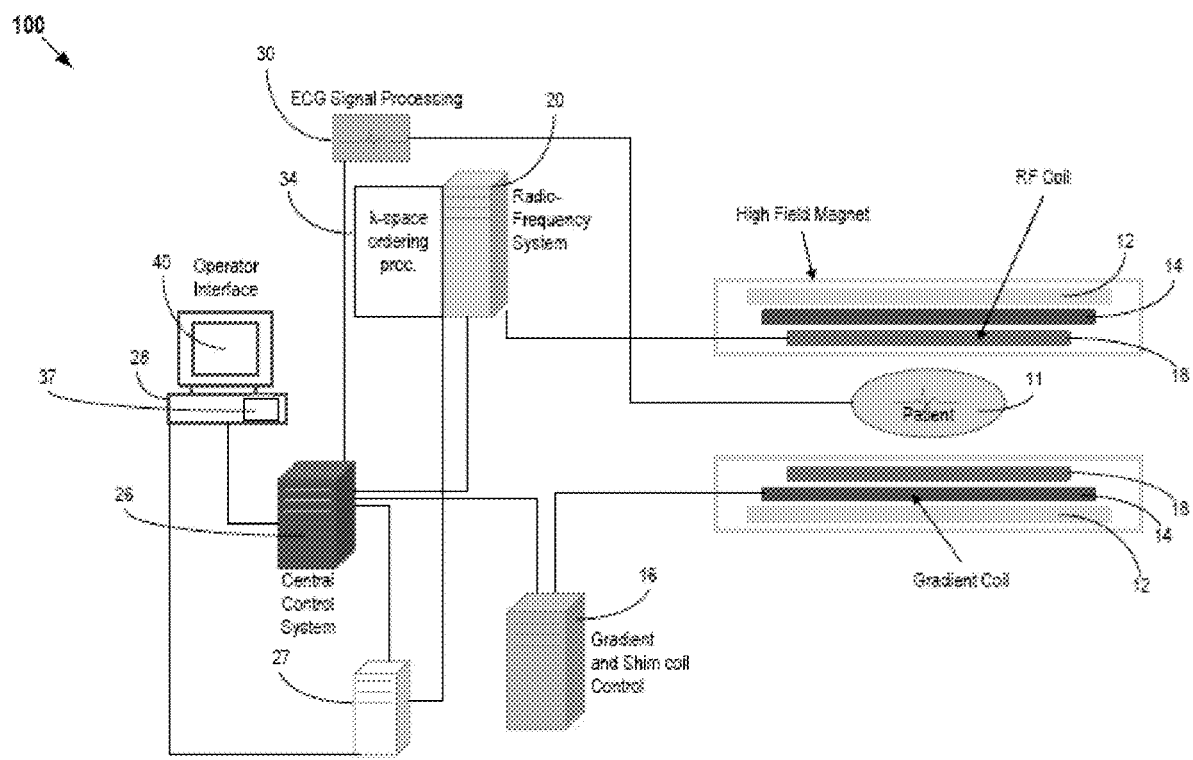
FIG. 1 is a block diagram of an embodiment of an MR system for medical imaging with repetition and reconstruction from the repetitions.

FIG. 1 shows one embodiment of a system for reconstruction in medical imaging. The system scans a given patient using a given protocol, creating repetitions of scan data having redundant information. The system applies a machine-learned model in reconstruction where the model is applied for different groups of scan data (e.g., each repetition) separately but was trained using a loss based on aggregation across groups.

The example used herein is in a MR context (i.e., a MR scanner), but the redundant scanning protocols and corresponding types of scanner may be used in reconstruction for CT, PET, SPECT, or other medical imaging.

The system uses a machine-learned model in reconstruction. The machine-learned model is formed from one or more networks and/or another machine-learned architecture (e.g., support vector machine). For example and used herein, the machine-learned model is a deep-learned neural network. The machine-learned model is used for at least part of the reconstruction, such as regularization of reconstruction. In regularization, image or object domain data is input, and image or object domain data with less artifact is output. The remaining portions or stages of the reconstruction (e.g., Fourier transform and gradients in iterative optimization) are performed using reconstruction algorithms and/or other machine-learned networks. In other embodiments, the machine-learned model with a loss based on aggregation is used for all the reconstruction operations (one model to input k-space data and output regularized image data) or other reconstruction operations (e.g., used for transform, gradient operation, and/or regularization). The reconstruction is of an object or image domain from projections or measurements in another domain, and the machine-learned model trained using loss from aggregation is used for at least part of the reconstruction.

The system is implemented by an MR scanner or system, a computer based on data obtained by MR scanning, a server, or another processor. MR scanning system 100 is only exemplary, and a variety of MR scanning systems can be used to collect the MR data. In the embodiment of FIG. 1, the system is or includes the MR scanner or MR system 100. The MR scanner 100 is configured to scan a patient. The scan provides scan data in a scan domain. The system 100 scans a patient to provide k-space measurements (measurements in the frequency domain). In a given scan or examination (e.g., imaging appointment), the patient is scanned multiple times as part of a protocol providing repetitions or groups of at least partly redundant information.

In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image (i.e., for reconstruction in the object domain from the k-space data in the scan domain). In some embodiments, the image data processor is in or is the central control unit 26. In other embodiments, such as the one depicted in FIG. 1, the image data processor is in a separate unit 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

The central control unit 26 uses information stored in an internal database to process the detected MR signals in a coordinated manner to generate high quality images of a selected slice(s) of the body (e.g., using the image data processor) and adjusts other parameters of the system 100. The stored information includes a predetermined pulse sequence of an imaging protocol and a magnetic field gradient and strength data as well as data indicating timing, orientation, and spatial volume of gradient magnetic fields to be applied in imaging.

The medical scanner 100 is configured by the imaging protocol to repetitively scan a region of a patient 11. The same patient 11, without leaving the scanner 100, is scanned in a repetitive manner, providing scan data in repetitions based on the protocol. For example, in MR, such protocols for scanning a patient for a given examination or appointment include diffusion-weighted imaging, turbo-spin-echo imaging, contrast imaging with different echo times, or contrast imaging with different flip angles. Other types of MR or non-MR protocols may use repetition. The sequential or other scanning results in a set of scan data grouped as two or more repetitions or scans.

The central control unit 26 (i.e., controller) and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used.

The image processor is configured by software, firmware, and/or hardware to reconstruct. The image processor operates pursuant to instructions stored on a non-transitory medium to perform various acts described herein.

The image processor is configured to reconstruct a representation in an object domain. The object domain is an image space and corresponds to the spatial distribution of the patient. A planar or volume representation is reconstructed as an image representing the patient. For example, pixels values representing tissue in an area or voxel values representing tissue distributed in a volume are generated.

The representation in the object domain is reconstructed from the scan data in the scan domain. The scan data is a set or frame of k-space data from a scan of the patient. The protocol for a scan of a patient may generate multiple such sets or frames of k-space (scan) data. For each repetition, the k-space measurements resulting from the scan sequence are transformed from the frequency domain to the spatial domain in reconstruction. In one approach, reconstruction for a given repetition is an iterative process, such as a minimization problem. In some embodiments, an unrolled iterative reconstruction is provided as a network or model of iteration sequences. A given iteration either in an unrolled network or through a repetition of the reconstruction operations includes a gradient update and regularization. The gradient update compares the current image object with the scan data (e.g., k-space measurements). This comparison uses a system transform to relate the measurements to the image object. Any gradient or comparison relating the image object to the measurements may be used. Regularization is provided in one, some, or all the iterations. Other filtering and/or operations for reconstruction and/or post-reconstruction may be provided. Input bias field correction and/or extrapolation for momentum may be provided as part of the reconstruction. In other embodiments, the reconstruction is performed without iteration.

The image processor is configured to reconstruct, for each of the repetitions, a representation of the region. The reconstruction uses application of a machine-learned model having been trained for the reconstruction for each of the repetitions based on a loss function between an aggregate of outputs from the repetitions of the protocol and a ground truth image. The training of the machine-learned model results in values for learnable (learned) parameters. By using the loss based on the aggregate image, object, or representation across repetitions to train the machine-learned model for reconstruction of a repetition, different values of the machine-learned model result than if a different loss where used.

The machine-learned model is repetitively used for the repetitions as a function in a deep set. The same machine-learned model is sequentially or in parallel applied in reconstruction for the different repetitions resulting from the imaging protocol. The machine-learned model is used in reconstruction from the scan data of one repetition and used in reconstruction from the scan data of another repetition. While the training used an aggregation across repetitions (e.g., average image from the different repetitions) for loss, the machine-learned model is applied to reconstruct the image for a given one of the repetitions or sub-group of repetitions at a time.

Since the machine-learned model is used for reconstruction of a given or each given repetition, a joint loss may have been used to train. The loss from the aggregation is combined with a loss for one or more repetitions to train. One loss is between the aggregate and the ground truth aggregate or final image, and another loss is between one or more of the representations for one or more of the repetitions and one or more ground truth images for respective one or more repetitions. Any combination of the two losses may be used, such as a weighted average.

The image processor is configured to reconstruct the representation (e.g., image or object) for each repetition. The machine-learned model is used for one, some, or each reconstruction from respective repetitions. The result is a set of reconstructed representations of the same region. The image processor is configured to combine the representations. Any motion correction and/or filtering may be used. The aligned representations are combined to form one representation of the region of the patient. For example, the combination is a sum (e.g., average), a geometric mean, or a geometric product. The diffusion-weighted imaging and turbo-spin-echo imaging protocols sum or average the representations. The contrast protocol may use the geometric mean or product. Other combinations of representations from different repetitions may be used, such as based on the imaging protocol.

The resulting representation may be a complex or real image. The output image is the final reconstructed image. The output image represents the patient (i.e., a reconstructed representation). The image processor may be configured to generate an MR image from the combined representation. Where the representation is of an area, the values of the representation may be mapped to display values (e.g., scalar values to display color values) and/or formatted (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

A generated image of the reconstructed representation (e.g., combined representation) for a given patient are presented on a display 40 of the operator interface. The computer 28 of the operator interface includes a graphical user interface (GUI) enabling user interaction with central control unit 26 and enables user modification of magnetic resonance imaging signals in substantially real time. The display processor 37 processes the magnetic resonance signals to provide image representative data for display on display 40, for example.

The display 40 is a CRT, LCD, plasma, projector, printer, or other display device. The display 40 is configured by loading an image to a display plane or buffer. The display 40 is configured to display the reconstructed MR image of the region of the patient.

Figure 2:
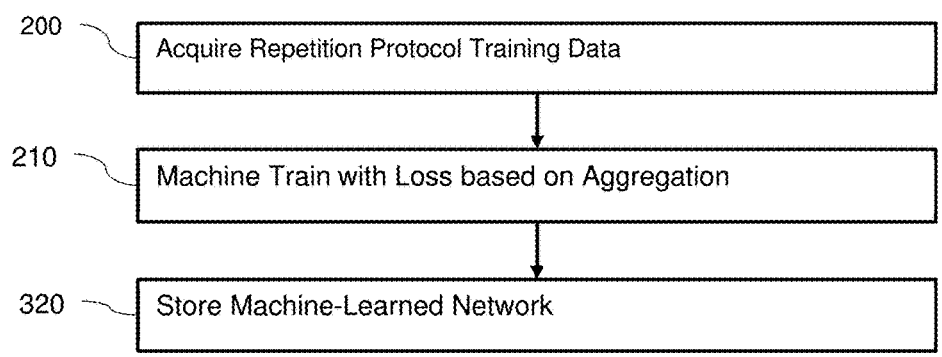
FIG. 2 is a flow chart diagram of one embodiment of a method for machine training for reconstruction using a loss function based on aggregation across repetitions.

FIG. 2 is a flow chart diagram of one embodiment of a method for machine training for reconstruction in medical imaging, such as training a neural network used in MR reconstruction from signals collected by an MR scanner. Once trained, the machine-learned model may be used with the same learned values in reconstruction of representations for any number of patients from a respective number of sets of MR scan data for the patients.

The method is implemented by a computer, such as a personal computer, workstation, and/or server. Other computers may be configured to perform the acts of FIG. 2. The MR scanner 100 or central control unit 26 may implement the method. In one embodiment, the computer and a database are used to machine train and store the samples and the resulting final trained model. The stored model is then distributed to one or more MR scanners 100 for application using the model as fixed (i.e., the learned values of the variables are not changed for reconstructions for a given patient and/or for different patients).

Figure 8:
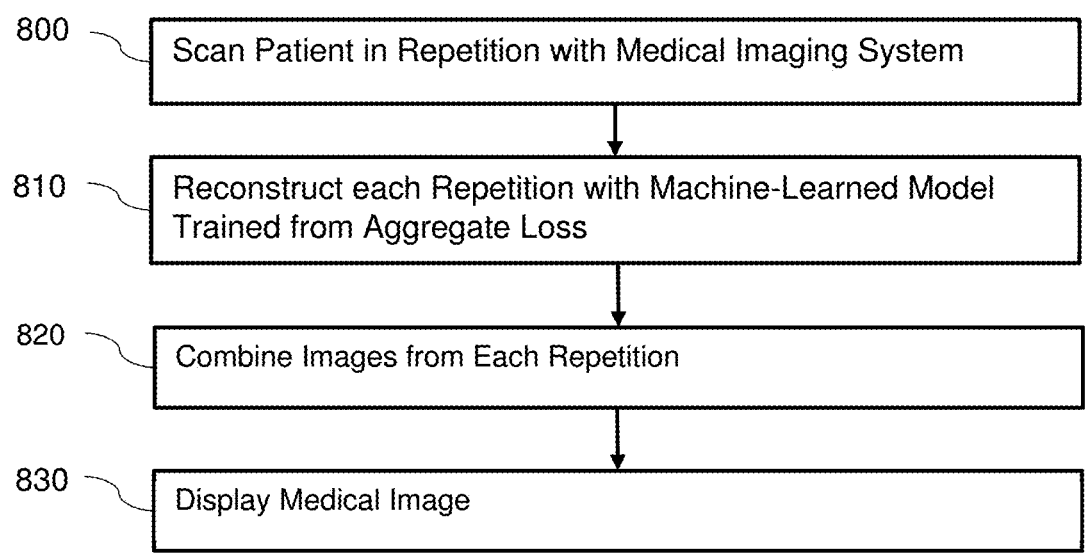
FIG. 8 is a flow chart diagram of one embodiment of a method for reconstruction using a machine-learned network having been trained from aggregate loss.

The method is performed in the order shown (i.e., top to bottom or numerical). Additional, different, or fewer acts may be provided. For example, instead of or in addition to storing in act 220, the machine-learned model is applied to previously unseen scan data for a patient in a reconstruction as shown in FIG. 8. As another example, an act for gathering or creating training data is performed.

In act 200, training data is acquired. The training data is acquired from memory, scanning, or transfer. To machine train, training data is created, gathered, or accessed.

The training data includes many sets of data, such as k-space data in sets where each set include multiple repetitions from a same scan sequence. Tens, hundreds, or thousands of sample scan data are acquired, such as from scans of patients, scans of phantoms, simulation of scanning, and/or by image processing to create further samples. Many examples that may result from different scan settings, patient anatomy, scanner characteristics, or other variance that results in different samples in scanning are used. In one embodiment, an already gathered or created MR dataset is used for the training data.

The samples are for scanning following a protocol that uses repetition, such as samples from diffusion-weighted, contrast (e.g., different echo times or flip angles), and/or turbo-spin-echo imaging. Depending on the role in reconstruction of the model to be machine trained, the training data may use k-space data or image domain data for the samples. The samples are used in deep learning to determine the values of the learnable variables (e.g., values for convolution kernels) that produce outputs with minimized cost function across the variance of the different samples.

The training data includes ground truth information. The desired representation or image resulting from a given sample is provided. For example, the final combined image from multiple repetitions without or with reduced artifacts to be output as a final image in reconstruction is provided as ground truth with some or all the samples of input being image or k-space data. As another example, ground truth images for each repetition for each set may be provided. These images may be combined to create a ground truth for the aggregation from the different repetitions and/or may be used respectively for losses based on given repetitions (e.g., where a joint loss for repetition and for aggregate is used).

In act 210, a computer (e.g., image processor) machine trains a model for reconstruction, such as training for a neural network for regularization, gradient, or k-space to final image operations. The neural network is machine trained for MR reconstruction using the training data, including many input samples of sets of scan data repetitions and corresponding ground truth outputs.

In one embodiment, deep learning is used to train the model. The training learns both the features of the input data and the conversion of those features to the desired output (i.e., denoised or regularized image domain data). Backpropagation, RMSprop, ADAM, or another optimization is used in learning the values of the learnable parameters of the network (e.g., the convolutional neural network (CNN) or fully connection network (FCN)). Where the training is supervised, the differences (e.g., L1, L2, mean square error, or other loss) between the estimated output and the ground truth output are minimized.

Any architecture or layer structure for machine learning to perform an operation for reconstruction may be used. For example, a hierarchal and/or iterative architecture to regularize in reconstruction may be used. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, and/or another network may be used. Some of the network may include dense blocks (i.e., multiple layers in sequence outputting to the next layer as well as the final layer in the dense block). Any know known or later developed neural network may be used. Any number of hidden layers may be provided between the input layer 301 and output layer 303. For iterative reconstruction, the architecture may include an unrolled arrangement of layers or iterative optimization.

The same network is trained to be used for each repetition. Alternatively, a different network is provided for each repetition, whether a different architecture or same architecture but with different values for one or more of the learnable parameters of the network. Different networks are trained for reconstruction for different repetitions.

The neural network is trained for MR reconstruction to output an image for each of the multiple repetitions. In response to input scan data of a repetition, the reconstruction outputs an image for that repetition. The network is to be trained to perform some aspect of this repetition-based reconstruction. As a result, an image may be output as an MR reconstruction for each of the multiple repetitions for a given protocol.

Figure 3:
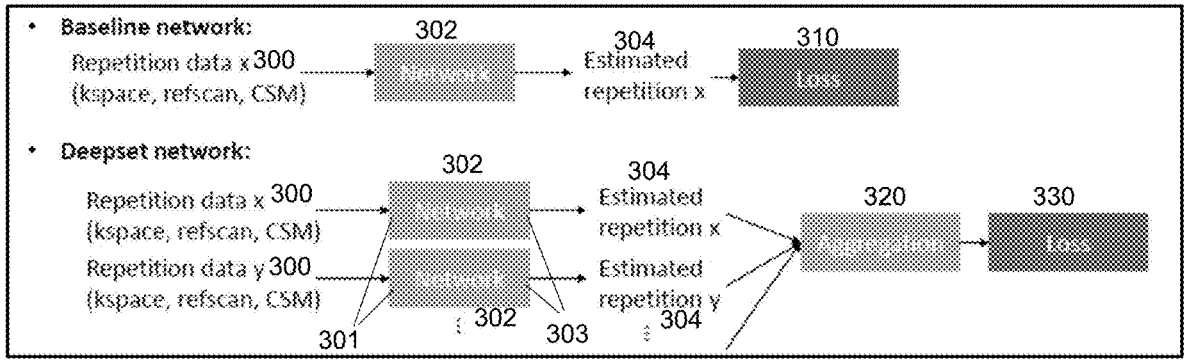
FIG. 3 illustrates example machine training of a network in a baseline approach of repetition-by-repetition and in an approach using aggregation across repetitions.

FIG. 3 shows an example. The baseline network 302 is trained to receive scan data 300 for a given repetition (e.g., repetition x) and output a representation 304 in response. The input may include other information, such as a reference scan, coil sensitivity map, and/or clinical measures for the patient. This same network 302 is trained to be applied for each of the repetitions (e.g., repetition y where scan data for x and y are acquired as part of a same scan of a same patient pursuant to the protocol).

In one embodiment, the network 302 is trained to output the image for each of the repetitions independently of the outputs or information for other ones of the repetitions. The scan data for repetition x, without the scan data for other repetitions, is used to reconstruct the image for repetition x. The scan data for repetition y, without the scan data for other repetitions, is used to reconstruct the image for repetition y. The input layer 301 of the network 302 is configured to accept the scan data for a single one of the repetitions to output the image for that single repetition.

Figure 4:
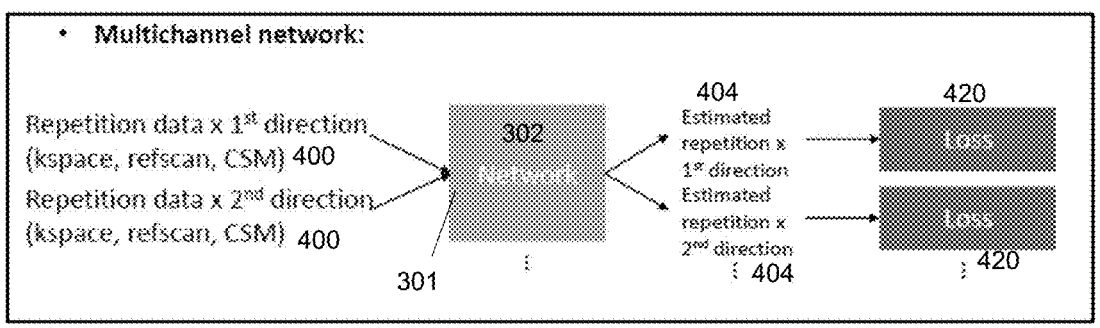
FIG. 4 illustrates example machine training a network in a baseline approach using multichannel input.

FIG. 4 shows another example. The input layer 301 includes multiple channels for scan data 400. Each channel is associated with a different direction within a given repetition rather than different repetitions. FIG. 4 shows use with different directions, but different contrasts may be used for this single-repetition, multi-channel network. The network 302 is to be trained for estimation of different images 404 for the different directions or contrasts for that given repetition. Other input channels may be provided, such as inputting patient clinical information.

The machine training uses a loss to learn the values of the learnable parameters. The loss is based, at least, in part, on an aggregation of the images from multiple repetitions. The training uses a loss function based on deep sets. Since repetition is provided in the protocol, the repetition may be used with the loss for training to reconstruct from a repetition. The repetitions can be sum-decomposable. Based on this, the architecture is designed where each repetition is fed into a neural network φ to provide a repetition reconstruction, then the results of the individual repetition reconstructions are aggregated in some way. The loss function, such as L1, is computed on the aggregated result for optimizing the values of the learnable parameters for the network. The resulting machine training of the neural network for repetition reconstruction preserves invariance by permutation with respect to the multiple repetitions.

FIG. 3 shows an example. Rather than using the baseline, the deepset network arrangement is used in training. The network 302 is applied in reconstruction for each of the repetitions (e.g., x, y, . . . ) of scan data 300, generating estimated images 304 for each of the repetitions (e.g., x, y, . . . ). The images 304 from the different repetitions are combined as the aggregation 320. The loss 330 is then based on this aggregation 320. The loss 330 is a measure of difference between the aggregation 320 of the images and a ground truth image such that the neural network 302 learns for each of the multiple repetitions based on the aggregation 320 across the multiple repetitions.

Figure 5:
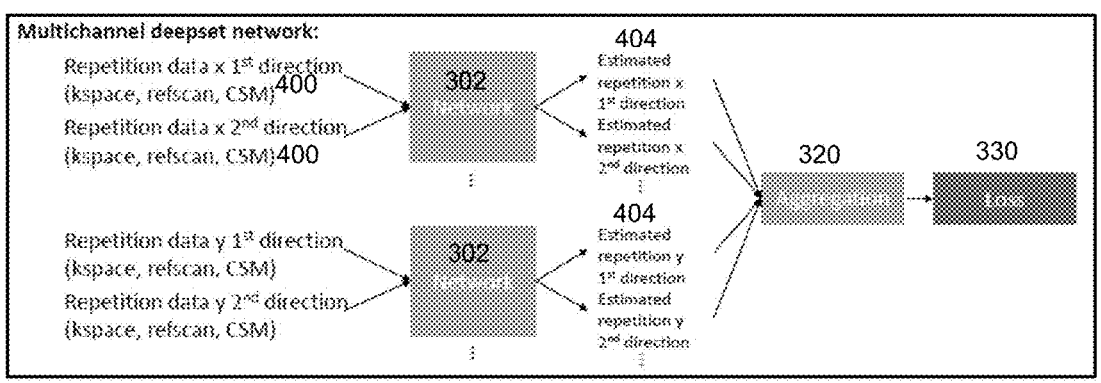
FIG. 5 illustrates example machine training a network with multichannel input using aggregation across repetitions.

FIG. 5 shows another example. The multi-channel network of FIG. 4 is used with aggregation 320. Instead of the repetition specific losses 420 of FIG. 4, the images 404 from the reconstructions for the different repetitions are aggregated. The images 404 from the different channels of each repetition 400 are included in the aggregation 320. This aggregation 320 is compared to the ground truth aggregation to provide the aggregation-based loss 330.

The aggregation is an average of the images. Other combinations may be used, such as weighted average. In other embodiments, the aggregation is a geometric mean or product, such as for combining images associated with different contrasts. Aggregation of individual averages (repetition images) can be performed in various ways. Examples are simple averaging of complex or magnitude images or combination of different diffusion directions (e.g., by calculating the geometric of different diffusion directions, known as calculation of "trace-weighted" images). Replacing a geometric mean (or a product) instead of a sum in Equation (1) is still valid as the equation can be re-written in the form of Equation (1) by changing functions ρ and φ with some log and exponentials (i.e., $\rho'(x)=\rho(e^{(x)})$, $\phi'(x)=\log(\phi(x))$. This construction follows the sum-decomposable form and is thus permutation invariant with respects to the repetitions.

Using a loss based on the aggregation from the images of different (all or a sub-set) repetitions creates a coupling between the different repetition reconstructions during the training. There is on the other hand no coupling during the inference procedure where the trained network is applied for each repetition prior to any aggregation. Each repetition can be reconstructed independently from each other as the acquisition goes on. This can enable a speed-up in the reconstruction (e.g., up to a possible real-time reconstruction) as each image can be reconstructed immediately after the scan data for that repetition has been acquired without having to wait for the completion of the next repetitions and/or the entire scan.

Figure 6:
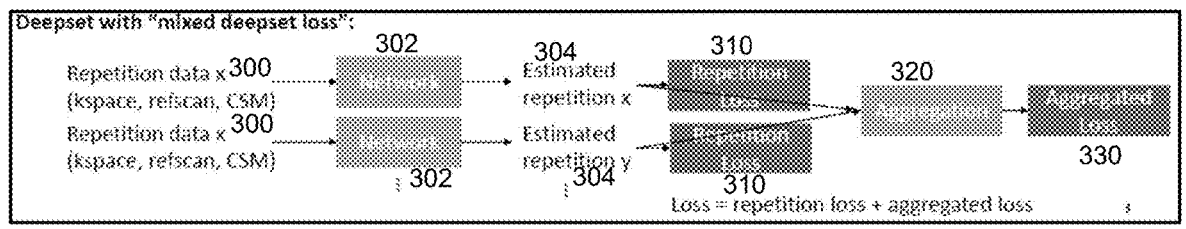
FIG. 6 illustrates example machine training a network with a joint loss by repetition and aggregation.
Figure 7:
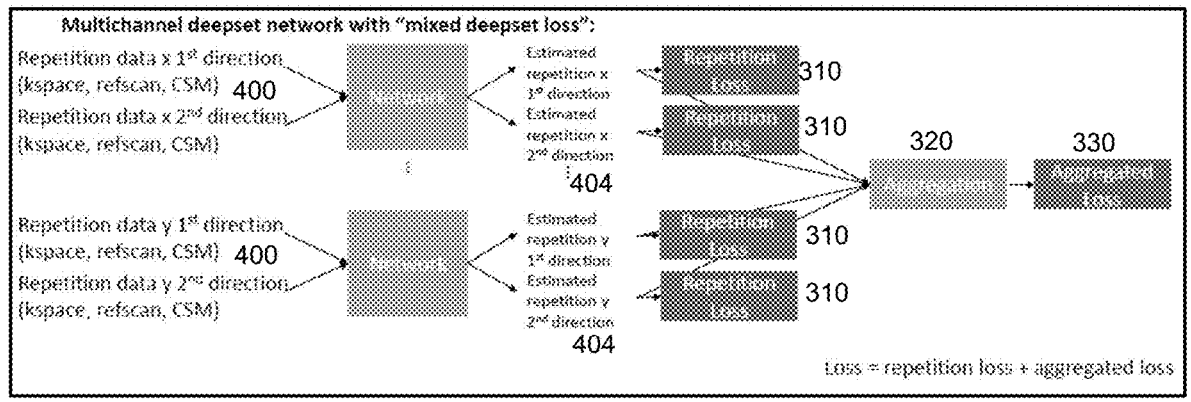
FIG. 7 illustrates example machine training a multichannel input network with a joint loss by repetition and aggregation.

In other embodiments, the loss based on the aggregation across repetitions is part of a joint loss. More than one loss is used in the training. For example, FIG. 6 shows the training approach of the deepset network of FIG. 3 with repetition-specific losses 310 (one for each repetition) in addition to the loss 330 based on the aggregation. As another example, FIG. 7 shows the training approach of the multi-channel deepset network of FIG. 5 with the repetition-specific losses 310 for each channel of each repetition (i.e., a loss 310 is calculated for each channel/direction/contrast of each repetition 400) and the loss 330 based on aggregation.

Any combination of losses may be used. For example, a weighted or simple average of the losses is used. In one embodiment, the relative weight of the individual repetition losses 310 and/or a sum of the repetition losses 310 is weighted equal to or with less weight than the loss 330 based on aggregation.

The network 302 is trained to be used in reconstruction separately or independently for each repetition. In other embodiments, one or more repetitions use information from other repetitions in reconstruction. For example, the neural network is trained to contribute to output the image for at least one of the multiple repetitions in dependence on information from the same neural network used to output an image for another one of the multiple repetitions. To increase the coupling between the repetition reconstructions, global operations that preserve equivariance between each repetition reconstruction are performed. The coupling is in addition to the aggregation loss 330, such as using values for features calculated in one repetition as inputs for another repetition. Pairs or other sub-sets of repetitions may be linked between repetitions in this way. In yet other embodiments, the output image from one repetition is used as input with the scan data for another repetition.

One such possible linking operation is a global pooling operating across the copies or instances of the network 302 used for each repetition reconstruction. For example, at different locations in the network 302, features across network copies (one copy per repetition) can be merged by adding a global pooling (e.g., max-pooling or averaged pooling) across the copies, followed by a concatenation layer of the local features (at each copy) and the result of the global pooling, followed by a 1×1 convolution that will merge (via a weighted sum) the local and global features.

Machine learning is an offline training phase where the goal is to identify an optimal set of values of learnable parameters of the model that can be applied to many different inputs. These machine-learned parameters can subsequently be used during clinical operation to reconstruct. Once learned, the machine-learned model is used in an online processing phase in which scan data from multiple repetitions are reconstructed into images. Once trained, the neural network is applied in reconstruction of a representation or image of a patient from a scan of that patient.

In act 220 of FIG. 2, the computer or image processor stores the machine-learned model resulting from the machine learning. For example, the network 302 is stored. The matrix or other parameterization of the machine-learned model is saved in memory. After training, the machine-learned model or models are represented as a matrix, filter kernels, and/or architecture with the learned values. The learned convolution kernels, weights, connections, and/or layers of the neural network or networks are provided and stored. The machine-learned model may be stored locally or transferred over a network or by moving the memory to other computers, workstations, and/or MR scanners.

The model resulting from the machine training using the plurality of the samples is stored. This stored model has fixed weights or values of learnable parameters determined based on the machine training. These weights or values are not altered by patient-to-patient or over multiple uses for different medical scans. The weights or values are fixed, at least over a number of uses and/or patients. The same weights or values are used for different scans corresponding to different patients and/or different examinations or appointments. The same values or weights may be used by different medical scanners. The fixed machine-learned model or models are to be applied without needing to train as part of the application. Re-training or updated training may be provided.

FIG. 8 is a flow chart diagram of one embodiment of a method for reconstruction of a medical image in a medical imaging system, such as reconstruction of a MR image in an MR system. A machine-learned model as trained is applied for at least part of the reconstruction operation for each of multiple repetitions of an imaging protocol. Once trained, the machine-learned model is used in reconstruction of a spatial representation from input k-space measurements for a patient. The application is part of scanning and reconstruction for patient diagnosis of a given patient for a given examination, scan, and/or appointment. The machine-learned model was previously trained using a loss based, at least in part, on an aggregation across the repetitions.

During application to one or more different patients and corresponding different scan data, the same learned weights or values are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The method is performed by the system of FIG. 1 or another system. The medical scanner scans the patient. An image processor reconstructs the image using the machine-trained model and combines images from the reconstructed images of the repetitions. A display displays the medical image resulting from the combination of images across repetitions. Other components may be used, such as a remote server or a workstation performing the reconstruction and/or display.

The method is performed in the order shown or other orders. Additional, different, or fewer acts may be provided. For example, a preset, default, or user input settings are used to configure the scanning prior art act 800. As another example, the image is stored in a memory (e.g., computerized patient medical record) or transmitted over a computer network instead of or in addition to the display of act 830.

In act 800, the medical imaging system scans a patient. The scan is guided by a protocol, such as diffusion-weighted, contrast, or turbo-spin-echo protocol. The scanning results in measurements over a series of scans in the imaging protocol. The pulse or scan sequence repetitively scans the same region of the patient, resulting in sets of scan data that may be independently or separately reconstructed to represent that region.

In an MR example, a pulse sequence is created based on the configuration of the MR scanner (e.g., the imaging protocol selected). The pulse sequence is transmitted from coils into the patient. The resulting responses are measured by receiving radio frequency signals at the same or different coils. The scanning results in k-space measurements as the scan data. Scan data for different repetitions is acquired. The scan includes scans for each repetition or over a series of scans.

In act 810, an image processor reconstructs representations of the patient from the scan data. The image processor reconstructs a representation for each scan (repetition) of a series of scans acquired following the protocol.

For MR reconstruction, the k-space data is Fourier transformed into scalar values representing different spatial locations, such as spatial locations representing a plane through or volume of a region in the patient. Scalar pixel or voxel values are reconstructed as the MR image. The spatial distribution of measurements in object or image space is formed. This spatial distribution represents the patient.

The reconstruction is performed, at least in part, using a machine-learned model, such as a neural network trained with deep machine learning. The machine-learned model is previously trained, and then used as trained in reconstruction for each of the scans of the series of scans defined by the protocol. Fixed values of learned parameters are used for application. In application of the already trained network, the reconstruction process is followed. The machine-learned model is used in the reconstruction for each repetition. In response to the input of the scan data for a given repetition for a given patient, a patient specific image is reconstructed. The machine-learned model may outputs the image as pixels, voxels, and/or a display formatted image in response to the input or be used in another way in the reconstruction. The learned values and network architecture, with any algorithms (e.g., extrapolation and gradient update) determine the output from the input.

The machine-learned model was previously trained for use for each scan (repetition) of the imaging protocol based on a loss function from a combination of training images from different scans for the imaging protocol. For example, the aggregation loss arrangement of FIG. 3, 5, 6, or 7 was used. The images from different repetitions of the protocol for which the network was trained are aggregated. The aggregated image is compared to a ground truth image to determine the loss used in the optimization to find the values of the learnable parameters of the model. The aggregation may be an average (e.g., sum), geometric mean, geometric product, or other combination used by a protocol using repetition.

Since the machine-learned model and corresponding reconstruction may be performed on each scan of the given protocol separately or independently, the reconstruction for each scan may be performed while another of the scans is occurring. A scan image for one of the scans of the series of scans in the pulse sequence is reconstructed prior to scanning of another of the scans of the series, such as reconstructing the initial scan during the second scan of the series and prior to the third or later scans of the series.

The output of the reconstruction, such the output of the machine-learned model, is a two-dimensional distribution of pixels representing an area of the patient and/or a three-dimensional distribution of voxels representing a volume of the patient. The output from the last reconstruction iteration may be used as the output representation of the patient for a given repetition.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

In act 820, the image processor combines the scan images into a medical image. The scan images from the different scans are combined, such as using the aggregation approach provided by the protocol. For example, the scan images (e.g., pixels or voxels) are averaged or summed as provided by diffusion-weighted or turbo-spin-echo protocols. The result is a medical image of the patient from the scanning for that appointment or examination.

The combination occurs after or before any rendering or reformatting for display. The representation or data derived from the reconstructed representations are combined. For example, voxels are combined prior to rendering. The scan images in the form of voxels representing a volume are combined. The resulting combination is then rendered to a two-dimensional display.

Other operations may be performed before, after, or during the combination. For example, spatial filtering is applied. As another example, the scan images are motion corrected or aligned spatially prior to combination.

In act 830, a display (e.g., display screen or device) displays the medical image, such as the MR image form by aggregation. The medical image, after or as part of any post processing, is formatted for display on the display. The display presents the image for viewing by the user, radiologist, physician, clinician, and/or patient. The image assists in diagnosis.

The displayed image may represent a planar region or area in the patient. Alternatively or additionally, the displayed image is a volume or surface rendering from voxels (three-dimensional distribution) to the two-dimensional display.

The same deep machine-learned model may be used for different patients. The same or different copies of the same machine-learned model are applied for different patients, resulting in reconstruction of patient-specific representations or reconstructions using the same values or weights of the learned parameters of the model. Different patients and/or the same patient at a different time may be scanned while the same or fixed trained machine-learned regularization model is used in reconstruction the image. Other copies of the same deep machine-learned model may be used for other patients with the same or different scan settings and corresponding sampling or under sampling in k-space.

By having used the loss based on aggregation in training the machine-learned model in reconstruction for individual repetitions, the resulting medical image (e.g., combined or aggregated image for a patient) may be better. For example, the diffusion-weighted imaging (DWI) protocol is used with the ipat2 sampling pattern and x2 average acceleration. One machine-learned model is trained to reconstruct in the baseline approach (using repetition loss 310) of FIG. 3, and another machine-learned model is trained to reconstruct in the deepset approach (using the loss 330 based on aggregation) of FIG. 3. The repetitions are averaged with half of the available repetitions of a typical acquisition to get the x2 acceleration of the acquisition.

In training, the baseline+DC (each repetition trained separately or independently with the network for each repetition including a final data-consistency layer) network 302 is trained on a dataset of liver and prostate samples with 1,300 k steps. The deepset with DC (loss based on aggregation with the network including a final data-consistency layer), with selection augmentation, is trained with 1,620 k steps. For selection augmentation, many different combinations of repetitions are generated from each given set for training. For example, there are 16 repetitions of one scan (i.e., one set of the many sets of training data). For training the network with the deepset approach, multiple different subsets of these repetitions are created to increase the number of samples. For example, the network is trained using subsets of 4,5,6,7, and 8 repetitions. For each subset, there are many ways to select, e.g., 4 repetitions out of the 16 available. Different procedures are used to select, increasing the number of training data samples. For example, one selection procedure is sequential (in the order acquired), another selection procedure is uniformly random, and another selection procedure is using a hierarchical algorithm to select the repetitions which are as similar as possible to each other (some may not be similar because of motion).

The peak signal-to-noise ratio (PSNR) is 28.11 for the baseline and 30.56 for the deepset, showing better performance for deepset approach. The structured similarity index (SSIM) is 0.8219 for the baseline and 0.84418, showing better performance for deepset approach. The zero-filled reconstruction input PSNR is 21.95 for both, and the zero-filled reconstruction input SSIM is 0.6850 for both.

Although the subject matter has been described in terms of exemplary embodiments, it is not limited thereto. Rather, the appended claims should be construed broadly, to include other variants and embodiments, which can be made by those skilled in the art.

What is claimed is:

1. A method of machine training for magnetic resonance (MR) reconstruction in medical imaging, the method comprising:
    acquiring training data for an MR protocol using multiple repetitions;
    machine training a neural network for the MR reconstruction using the training data, the neural network training for the MR reconstruction to output an image for each one of the multiple repetitions, a first loss used in the training being based on an aggregation of the images from the multiple repetitions, the first loss comprising a measure of difference between the aggregation of the images and a ground truth image such that the neural network learns for each of the multiple repetitions based on the aggregation across the multiple repetitions; and
    storing the neural network as machine trained.

2. The method of claim 1 wherein machine training comprises training the neural network to output the image for each one of the multiple repetitions independently of the output for other ones of the multiple repetitions.

3. The method of claim 1 wherein machine training comprises training the neural network to output the image for at least one of the multiple repetitions in dependence on information from the neural network used to output an image for another one of the multiple repetitions.

4. The method of claim 3 wherein the dependence comprises a global pooling across instances of the neural network for respective ones of the multiple repetitions.

5. The method of claim 1 wherein acquiring the training data comprises acquiring with the MR protocol being a diffusion-weighted, turbo-spin-echo, contrast with different echo times, or contrast with different flip angles protocol.

6. The method of claim 1 wherein machine training comprises machine training the neural network for repetition reconstruction preserving invariance by permutation with respect to the multiple repetitions.

7. The method of claim 1 wherein machine training comprises machine training where the aggregation is an average, a geometric product, or a geometric mean.

8. The method of claim 1 wherein the neural network comprises an input layer configured to accept information for a single one of the multiple repetitions for the output of the image for that single one of the multiple repetitions.

9. The method of claim 1 wherein the neural network comprises an input layer having separate inputs of different directions or contrasts, and wherein the training is to output the image from the different directions or contrasts for each of the multiple repetitions.

10. The method of claim 9 wherein machine training comprises applying a joint loss of the first loss based on the aggregation and a repetition loss for each of the different directions or contrasts of each of the multiple repetitions.

11. The method of claim 1 wherein machine training comprises applying a joint loss of the first loss based on the aggregation and a repetition loss each image for each of the multiple repetitions.

12. A method for reconstruction of a medical image in a medical imaging system, the method comprising:
scanning, by the medical imaging system, a patient, the scanning resulting in measurements over a series of scans of an imaging protocol;
reconstructing, by an image processor applying a machine-learned model, a scan image for each of the scans of the series, the machine-learned model having been trained for use for each scan of the imaging protocol based on a loss function from a combination of training images from different scans for the imaging protocol, the loss function comprising a difference between the combination of the training images and a ground truth image;
combining the scan images into the medical image; and
displaying the medical image.

13. The method of claim 12 wherein scanning comprises magnetic resonance scanning with the imaging protocol comprising a diffusion-weighted imaging protocol or a turbo-spin-echo imaging protocol, and wherein the combination used to train is an average.

14. The method of claim 12 wherein reconstructing the scan image for one of the scans of the series occurs prior to the scanning for another of the scans of the series.

15. A system for reconstruction in medical imaging, the system comprising:
a medical scanner configured to repetitively scan a region of a patient pursuant to a protocol, the scan providing scan data in repetitions of the protocol;
an image processor configured to reconstruct, for each of the repetitions, a representation of the region, the image processor configured to reconstruct by application of a machine-learned model having been trained for the reconstruction for each of the repetitions based on a loss function of a difference between an aggregate of outputs from the repetitions of the protocol and a ground truth, the image processor further configured to combine the representations from the repetitions; and
a display configured to display an image of the region from the combined representations.

16. The system of claim 15 wherein the medical scanner comprises a magnetic resonance scanner, wherein protocol comprises a diffusion-weighted, turbo-spin-echo, or contrast protocol, and wherein the combination of representations comprises a sum, a geometric mean, or a geometric product.

17. The system of claim 15 wherein the machine-learned model comprises a neural network and wherein the neural network is repetitively used for the repetitions as a function in a deep set.

18. The system of claim 15 wherein the loss function comprised a joint loss of first and second losses, the first loss being between the aggregate and the ground truth and the second loss being between one of the representations for one of the repetitions and another ground truth.

* * * * *